United States Patent [19]

Crocco et al.

[11] Patent Number: 5,599,987
[45] Date of Patent: Feb. 4, 1997

[54] INTEGRATED PROCESS FOR CYCLOHEXANONE OXIME PRODUCTION

[75] Inventors: Guy L. Crocco, Wilmington, Del.; John C. Jubin, Jr., West Chester; John G. Zajacek, Devon, both of Pa.

[73] Assignee: Arco Chemical Technology, L.P., Greenville, Del.

[21] Appl. No.: 414,677

[22] Filed: Mar. 31, 1995

[51] Int. Cl.$^6$ .................... C07C 249/04; C07D 201/02; C07D 201/04; C07D 201/06
[52] U.S. Cl. ................ 564/267; 540/335; 540/336
[58] Field of Search .................. 564/267; 540/335, 540/336

[56] References Cited

U.S. PATENT DOCUMENTS

| | | | |
|---|---|---|---|
| 2,819,949 | 1/1958 | Keeler et al. | 23/207 |
| 2,869,989 | 1/1959 | Keeler et al. | 23/207 |
| 2,871,104 | 1/1959 | Rust | 23/207 |
| 2,949,343 | 8/1960 | Hood et al. | 23/207 |
| 4,745,221 | 5/1988 | Roffia et al. | 564/267 |
| 4,794,198 | 12/1988 | Roffia et al. | 564/267 |
| 4,894,478 | 1/1990 | Roffin et al. | 564/267 |
| 5,041,652 | 8/1991 | Padovan et al. | 564/267 |

OTHER PUBLICATIONS

Roffia et al, "Cyclohexanone Ammoximation: A Breakthrough in the 6– Caprolactam Production Process", *New Developments in Selective Oxidation* G. Centi and Trifiro eds. Elsevier, 1990, pp. 43–52.
Roffia et al., "A New Process for Cyclohexanonoxime", *La Chimica & L' Industrin* 72, 598–603 (1990).
Reddy et al., "Ammoximation of Cyclohexamine . . . ", *J. Mol. Catal.*, 69, 383–392 (1991).
Clerici, "Catalytic Oxidation with Hydrogen Peroxide . . . ", in *Heterogenous Catalysis and fine Chemicals III*, M. Guismet et al., eds. Elsevier, pp. 21–33, 1993.

*Primary Examiner*—Peter O'Sullivan
*Attorney, Agent, or Firm*—Stephen D. Harper

[57] ABSTRACT

An integrated process for producing cyclohexanone oxime, a caprolactam precursor, is provided wherein isopropanol is utilized to generate the hydrogen peroxide oxidizing agent. The acetone produced as a co-product is recycled back to the secondary alcohol by hydrogenation. Ammoximation of cyclohexanone is performed in the presence of water and an alcohol other than isopropanol such as methanol or t-butyl alcohol.

15 Claims, 1 Drawing Sheet

INTEGRATED PROCESS FOR CYCLOHEXANONE OXIME PRODUCTION

FIELD OF THE INVENTION

This invention relates to an efficient method for obtaining cyclohexanone oxime.

BACKGROUND OF THE INVENTION

Caprolactam, which is employed in the production of nylon-6, may be derived from cyclohexanone oxime via an acid-catalyzed Beckmann rearrangement. At the present time, commercial processes for producing cyclohexanone oxime include the reaction of cyclohexanone with hydroxylamine sulfate and ammonia. Such a process is not ideal since it generates sulfate salt by-products and requires numerous steps. Improved procedures for producing cyclohexanone oxime therefore would be highly desirable.

SUMMARY OF THE INVENTION

The invention furnishes an integrated process for producing cyclohexanone oxime wherein isopropanol is reacted with molecular oxygen in a liquid phase at a temperature of from 50° C. to 200° C. to form an oxidant mixture comprised of isopropanol, acetone, and hydrogen peroxide. Substantially all of the acetone and all of the isopropanol are separated from the oxidant mixture so as to provide a stream comprising hydrogen peroxide and water, but essentially free of acetone (e.g., less than 1 wt. %), isopropanol (e.g., less than 1 wt %) and ketone peroxides (e.g., less than 0.5 wt. %). Such separation may be effected by distillation wherein an amount of water is introduced during such distillation sufficient to maintain the hydrogen peroxide concentration below 50% by weight (preferably, less than 30% if appreciable quantities of organic compounds are present). The acetone separated from the oxidant mixture is reacted with hydrogen in the presence of a heterogeneous hydrogenation catalyst wherein said catalyst is comprised of a transition metal selected from nickel, chromium, platinum, ruthenium, rhodium, and palladium at a temperature of from 20° C. to 175° C. and a hydrogen pressure of from 0.5 to 100 atmospheres. The acetone is thereby converted back to isopropanol which may be readily recycled for further use in generating additional quantities of hydrogen peroxide. The aqueous hydrogen peroxide stream is utilized as a source of hydrogen peroxide in the reaction of cyclohexanone with ammonia wherein an alcohol solvent such as methanol or t-butyl alcohol is additionally present in an amount sufficient to form a single liquid phase reaction mixture. A titanium silicalite catalyst serves to catalyze the cyclohexanone reaction. The alcohol present in the ammoximation reaction product is recovered by a suitable means such as distillation, either before or after conversion of the oxime to caprolactam and recycled back to the ammoximation step of the process.

A key advantage of the process of this invention is that selectivity to cyclohexanone oxime is greatly enhanced by removing both the acetone and isopropanol from a hydrogen peroxide-containing oxidant mixture prior to use of such mixture in cyclohexanone ammoximation. Separation of the acetone from the oxidant mixture has also been found to minimize the accumulation of organic peroxy species resulting from the interaction of acetone and hydrogen peroxide. Moreover, such removal has been found to be effective in liberating hydrogen peroxide from any ketone peroxide generated during oxidation of the isopropanol or subsequent storage. Such peroxy species lower the overall efficiency of the process since hydrogen peroxide is being consumed and may complicate the purification or separation steps. Organic peroxides derived from acetone and hydrogen peroxide are known to be dangerously explosive (see, for example, Milas et al., *J. Am. Chem. Soc.* 81, 6461–6462 (1959)). Such ketone peroxides will tend to accumulate during secondary alcohol oxidation, during storage of the oxidant mixture, as well as during cyclohexanone ammoximation. In this context, the term "ketone peroxides" includes those organic compounds derived from interaction of the acetone and hydrogen peroxide which contain at least one —O—O group (see for example, Sauer et al., *Physical Chem.* 75, 3004–3011 (1971) and Sauer et al., ibid. 76, 1283–1288 (1972)). Removal of the isopropanol from the oxidant mixture has also been found to be surprisingly beneficial. Isopropanol may be present in a titanium silicalite-catalyzed epoxidation of an olefin without significant effect on epoxide selectivity (see U.S. Pat. No. 5,384,418). However, during cyclohexanone ammoximation, oxidation of the isopropanol to acetone competes to some degree with the desired reaction of cyclohexanone resulting in non-selective losses of hydrogen peroxide. Yields of cyclohexanone oxime thus are maximized if neither isopropanol or acetone is present to any significant extent during ammoximation.

The acetone which is separated from the oxidant mixture may be readily transformed back to isopropanol by hydrogenation; the instant process thus is highly desirable from a commercial point of view since no substantial quantities of organic co-products are generated. Moreover, the only co-product which is produced (water) may be readily disposed of without significant environmental impact. The net overall reaction may be represented as follows:

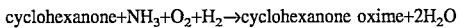

cyclohexanone+NH$_3$+O$_2$+H$_2$→cyclohexanone oxime+2H$_2$O wherein the oxime is the only organic species produced (other than minor quantities of by-products) and cyclohexanone is the only organic species consumed.

DETAILED DESCRIPTION OF THE INVENTION

A. Isopropanol Oxidation

Figure 1:
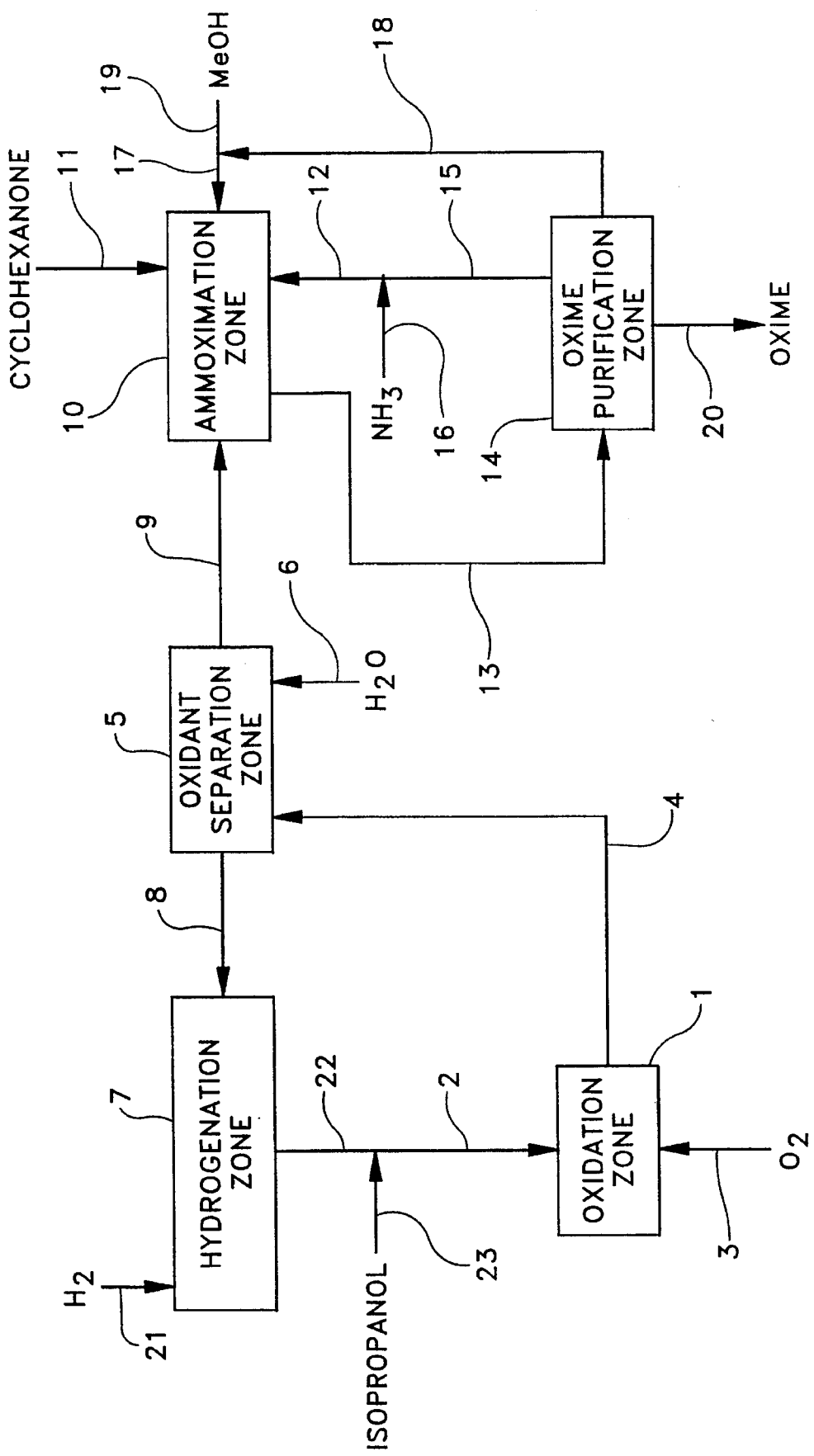
FIG. 1 illustrates one embodiment of the integrated ammoximation process of this invention wherein cyclohexanone is converted to cyclohexanone oxime.

Isopropanol is reacted with molecular oxygen from a suitable source such as air to yield an oxidant mixture. The isopropanol to be oxidized may contain minor amounts of acetone and/or water. For example, the azeotrope of water and isopropanol may be advantageously used. Methods of oxidizing secondary alcohols with molecular oxygen so as to obtain mixtures of hydrogen peroxide, ketone, and secondary alcohol are well-known in the art and are described, for example, in U.S. Pat. Nos. 2,819,949, 2,871,102, 2,871,103, and 2,479,111, and British Pat. Nos. 758,907, and 1,421,499, the teachings of which are incorporated herein by reference in their entirety. The reaction is preferably carried out in the liquid phase at a temperature of from 50° to 200° C. (more preferably, from 100° to 180° C.). Only partial conversion of the isopropanol (e.g., about 5 to 50%) is achieved. Residence, hold-up or reaction times of from about 0.25 to 4 hours will typically be sufficient for this purpose. The preferred range of oxygen partial pressure in the feed gases (which may include an inert diluent gas such as nitrogen in addition to oxygen) is 1 to 50 psia (more preferably, 5 to 15 psia) partial pressure. For safety reasons, the explosive range should be avoided. The hydrogen peroxide generated remains, collects, or accumulates in the liquid body comprised of isopropanol that is undergoing oxidation. A small amount of hydrogen peroxide, organic peroxide or hydroperoxide can be used in the initial oxidation reaction mixture, particularly when a highly purified isopropanol stream is utilized as a feed. Although this isopropanol oxidation does not require the presence of an added catalyst, such a catalyst may be used if so desired as disclosed, for example, in U.S. Pat. No. 2,910,415 and British Pat. No. 871,830 (the teachings of which are incorporated herein by reference in their entirety). Materials which promote the decomposition of the hydrogen peroxide produced should be scrupulously excluded from the reaction zone within which the oxidation is conducted. Hydrogen peroxide stabilizers may be added, although care should be taken to avoid substances which may inhibit or otherwise detrimentally affect the subsequent ammoximation reaction. The oxidant mixture generated by reacting the isopropanol will typically contain about one equivalent of hydrogen peroxide and one equivalent of acetone for every equivalent of isopropanol which has been consumed. Such a mixture thus will usually have the following composition: 40–90 weight % unreacted isopropanol, 5 to 35 weight % acetone, 1 to 25 weight % hydrogen peroxide, and 0 to 35 weight % water. The isopropanol oxidation can be carried out continuously (using, for instance, a continuous stirred tank reactor) or batchwise. A plurality of oxidation reaction zones maintained at different temperatures may be employed as described in British Pat. No. 758,907.

B. Isopropanol/Acetone Separation Step

Prior to use of the oxidant mixture in the ammoximation step of this invention, it is critical that the acetone and the isopropanol be substantially separated or removed from the oxidant mixture, with the amount of water present being adjusted such that the concentration of hydrogen peroxide in the mixture does not exceed 50%. Preferably, the $H_2O_2$ concentration should not 30% if any appreciable level of organic compounds is present. Any known separation method or technique which is suitable for this purpose may be utilized, including fractionation procedures.

Particularly suitable for use for this purpose are the methods described in U.S. Pat. Nos. 2,819,949 (Keeler et al.), 2,869,989 (Keeler et al.), 2,871,104 (Rust), and 2,949,343 (Hood et al.), the teachings of which are incorporated herein by reference in their entirety.

One suitable method involves dilution of the oxidant mixture with a volume of water sufficient to provide the desired final $H_2O_2$ concentration, followed by removal of the acetone and isopropanol by distillation. The hydrogen peroxide is thereby obtained as an aqueous solution in the form of a bottoms fraction. Generally, it will be advantageous to control the conditions of the distillation such that the active oxygen (peroxy oxygen)-containing species other than hydrogen peroxide which may be present in the oxidant mixture, such as the ketone peroxides previously described, are selectively decomposed to hydrogen peroxide. For example, the oxidant mixture may be subjected to a controlled heat treatment and to a continuous rectification in a fractionating column under controlled conditions of column operation and rate of throughput of the feed to the column. The heat treatment and rectification are desirably carried out concurrently, or simultaneously, in a rectification zone whereby in the one operation selective decomposition of the combined peroxygen to hydrogen peroxide and recovery of unconsumed isopropanol, acetone, and, separately, an aqueous solution of hydrogen peroxide are achieved. Such a process may comprise introducing a stream of oxidant mixture into an upper portion of a fractionating column comprising a stripping zone wherein there is maintained an absolute pressure within the range of 400 to 700 mm Hg. A stream of water is introduced into a lower portion of said fractionating column. A liquid portion of the streams flows downwardly through the stripping zone in substantial vapor-liquid equilibria with ascending vapors evolved therefrom under constant conditions of refluxing and reboiling. A vaporous mixture of isopropanol, acetone, and water is continuously withdrawn overhead from the stripping zone (below the point of introduction of the water stream). An aqueous solution of hydrogen peroxide is continuously withdrawn from a bottom part of the stripping zone. The rates of withdrawal of the vaporous mixture and the aqueous solution are adjusted so as to provide a substantially constant residence time within the stripping zone of the descending liquid portion of the feed of from about 10 to 80 minutes. The feed to the column should contain an amount of water such that the aqueous hydrogen peroxide stream from the column preferably contains from 5 to 50% by weight, more preferably from 10 to 30% by weight, of hydrogen peroxide. Typically, this will mean that the amount of water fed to the column will be from about 50 to 100% of the total weight of acetone, isopropanol, and $H_2O_2$ in the oxidant mixture.

C. Hydrogenation Step

The acetone removed from the oxidant is hydrogenated to isopropanol and the isopropanol which is thereby generated recycled at least in part to the oxidation step of the process. Such hydrogenation may be performed upon a stream containing relatively pure acetone or, if preferred, upon a stream comprised of acetone and isopropanol and/or water, as the hydrogenation conditions may be selected such that the presence of the latter two materials does not interfere with the desired reduction of the acetone. Thus, the acetone, isopropanol, and water separated from the oxidant mixture may be fractionated prior to the hydrogenation step or simply carried forward together into hydrogenation. Methods of converting acetone by catalytic hydrogenation using a transition metal catalyst and hydrogen gas are well-known. While optimum hydrogenation conditions will vary somewhat depending upon the particular metallic catalyst selected for use and may be readily ascertained by routine experimentation, generally speaking temperatures of from 20° to 175° C. and hydrogen pressures of from 0.5 to 100 atmospheres will suffice. Preferably, the molar ratio of $H_2$ to acetone is from about 1:1 to 4:1. Catalyst concentrations of from about 0.1 to 10 weight percent based on the weight of the acetone-containing stream will generally be suitable. The amount of catalyst employed is preferably sufficient to permit weight hourly space velocities of from 0.1 to 10 grams of acetone per gram of catalyst per hour. The reaction conditions should be chosen so as to avoid substantial over-reduction of the acetone to alkane.

The transition metal in the hydrogenation catalyst is most preferably palladium, platinum, chromium (as in copper chromite, for example), rhodium, nickel, or ruthenium. If water is present in the overhead stream, the use of Raney nickel or molybdenum-promoted nickel is especially advantageous. The hydrogenation is suitably carried out in either a liquid or vapor phase.

D. Ammoximation Step

The aqueous hydrogen peroxide stream containing hydrogen peroxide and water but little or no acetone and isopropanol, is reacted with cyclohexanone and ammonia using titanium silicalite as a catalyst. Reactions of this type are well known in the art. Suitable titanium silicalite catalysts for this purpose, which can be broadly described as porous crystalline molecular sieves (zeolites) containing Si, Ti, and, optionally, minor amounts of other elements (e.g., Al, B, Fe) in their framework structures are also well known. Titanium silicalites are also at times referred to in the literature as titanium silicates and titanosilicates.

Particularly preferred titanium silicalites include the classes of molecular sieves commonly referred to as "TS-1" (having an MFI topology analogous to that of the ZSM-5 aluminisilicate zeolites) and "TS-2" (having an MEL topology analogous to that of the ZSM-11 aluminosilicate zeolites). Also suitable for use are titanium-containing molecular sieves having framework structures isomorphous to zeolite beta. The titanium silicalite may contain minor amounts of elements other than titanium and silica in the lattice framework, such as, for example, aluminum, iron, boron, and the like. The titanium silicalite may be preactivated by treating with hydrogen peroxide and/or acid.

Ammoximation catalysts suitable for use in this invention will typically have a composition corresponding to the empirical formula $xTiO_2:(1-x)SiO_2$, where x is between 0.0001 and 0.500 (although, as mentioned previously, other elements such as Al may additionally be present). More preferably, the value of x is from 0.01 to 0.125. The use of a silicalite containing a relatively high level of titanium, i.e., where x is greater than 0.04, may be advantageous. The molar ratio of Si:Ti in the lattice framework of the titanium silicalite is desirably from 9.5:1 to 99:1 (more preferably, from 9.5:1 to 70:1).

The titanium silicalite catalyst may be utilized in powder, pellet, extruded, microspheric, monolithic or any other suitable physical form. The use of a binder (co-gel) or support in combination with the titanium silicalite may be advantageous. The ammoximation is desirably performed at a temperature of from 25° C. to 150° C. (more preferably, 50° C. to 125° C.). The synthesis can be carried out either continuously or discontinuously, provided reactors are used whose surfaces are consistent with hydrogen peroxide and ammonia. When the synthesis is carried out in batchwise fashion, it is advisable to use from 0.1 to 50 parts by weight (preferably from 1 to 20 pads by weight) of pure catalyst (binder excluded) for 100 parts by weight of cyclohexanone. If it is performed in a continuous mode, it is suggested to employ a space velocity from 0.1 to 200 kg/h of cyclohexanone ($C_6H_{10}O$) per kg of catalyst. The $H_2O_2$:$C_6H_{10}O$ molar ratio generally ranges from 0.5 to 2.5 and preferably from 0.8 to 1.5.

The ammonia is preferably added before the hydrogen peroxide, preferably in molar excess relative to the quantity of cyclohexanone (generally, at least 1.5 moles of ammonia per mole of cyclohexanone). Reaction times for the ammoximation preferably range from about 0.25 to 12 hours. The titanium silicalite catalyst can be arranged on a fixed bed or can be finely dispersed or suspended in the reaction medium. Regeneration or reactivation of the titanium silicalite by means of calcination, solvent treatment, base treatment, peroxide treatment, acid treatment or the like may be advantageous. Suitable reactors in which the ammoximation may be conducted include isothermal slurry reactors, transport bed reactors, continuous stirred tank reactors and adiabatic trickle-bed reactors. The reaction may be carried out at atmospheric pressure or, preferably, at a somewhat higher pressure in order to keep a quantity of ammonia at least equal to that required for the ammoximation dissolved in the reaction medium.

An alcohol selected from methanol, t-butyl alcohol, or mixtures thereof is also present during ammoximation for the purpose of solubilizing the cyclohexanone in the aqueous hydrogen peroxide stream. A single liquid phase reaction mixture is thereby established. The alcohol thus serves to enhance the commercial operability of the process since the presence of a biphasic reaction mixture may complicate implementation on a large scale, yet can be readily recovered from the oxime product when desired. The amount of alcohol may vary substantially, with concentrations of from about 10 to 75 weight percent (based on the total amount of alcohol, cyclohexanone, and aqueous hydrogen peroxide stream) being preferred. The proportion of water:alcohol may advantageously be from 2:1 to 1:2. The manner in which the alcohol is introduced is not critical. For example, the alcohol may be introduced as a separate stream or combined with the cyclohexanone or the aqueous hydrogen peroxide stream.

At the end of the ammoximation reaction, which typically is carried out such that a high degree of cyclohexanone conversion (e.g., over 75%) is achieved, the cyclohexanone oxime can be separated and purified by any suitable method such as, for example, extraction or distillation or may, if desired, be directly converted without isolation to caprolactam using known procedures such as sulfuric acid-catalyzed rearrangement. A vapor phase Beckman rearrangement of the cyclohexanone oxime catalyzed by titanium silicalite or the like could also be practiced. The alcohol may be recovered from the ammoximation reaction product (either before or after conversion of the oxime to caprolactam) by any appropriate method such as fractional distillation or the like and recycled for use in the ammoximation step of the instant process.

FIG. 1 illustrates one embodiment of the integrated ammoximation process of this invention wherein cyclohexanone is converted to cyclohexanone oxime. A stream comprised of isopropanol passes via line 2 into oxidation zone 1 wherein the isopropanol is reacted with molecular oxygen to form an oxidant mixture comprised of hydrogen peroxide, acetone, and excess isopropanol. The molecular oxygen may be provided by air, pure oxygen, or a synthetic mixture of $O_2$ and an inert gas such as nitrogen introduced via line 3.

The oxidant mixture containing hydrogen peroxide passes from zone 1 via line 4 into oxidant separation zone 5. In 5, the oxidant mixture is subjected to distillation or other such separation procedure capable of removing acetone and isopropanol from the mixture. If the original oxidant mixture contains an insufficient quantity of water relative to the final $H_2O_2$ concentration desired in the aqueous hydrogen peroxide stream withdrawn from zone 5, additional water may be introduced via line 6, or, alternatively, may be fed into line 4 to dilute the oxidant mixture before it enters the oxidant separation zone. Acetone and isopropanol (typically, together with some water, but little or no hydrogen peroxide) may, for example, be taken overhead into hydrogenation zone 7 via line 8. The overhead stream exiting zone 5 in gaseous form is preferably condensed into liquid form prior to or upon entering zone 7; alternatively, the overhead stream may be maintained in gaseous form while being hydrogenated (i.e., a vapor phase hydrogenation may be performed). The aqueous hydrogen peroxide stream from zone 5, which may be a bottoms fraction and which contains hydrogen peroxide and water but essentially no acetone, isopropanol or ketone peroxides, is introduced via line 9 into cyclohexanone ammoximation zone 10.

The cyclohexanone to be ammoximated is fed into ammoximation zone 10 via line 11. The titanium silicalite catalyst may be introduced via a separate line or, alternatively, deployed in zone 10 as a fixed bed. Ammonia may be introduced to zone 10 via line 12 or, if desired, via line 11 in admixture with cyclohexanone. An alcohol such as methanol, t-butyl alcohol, or a mixture of such alcohols may be introduced through line 17 to serve as a diluent and/or solubilizing agent during ammoximation. The resulting reaction mixture is maintained at the desired temperature and pressure in zone 10 for a time sufficient to convert at least a portion, and preferably at least about 75%, of the cyclohexanone to cyclohexanone oxime, thereby consuming a portion of the hydrogen peroxide (which is converted to water). Preferably, substantially all of the hydrogen peroxide (e.g., at least 90%, most preferably, at least 98%) is reacted. The crude ammoximation product thus generated passes through line 13 to oxime purification zone 14. Any of a number of different purification methods may be practiced in zone 14. For example, the crude ammoximation product may be subjected to fractional distillation to remove species more volatile than water. Any unreacted ammonia removed in this fashion may be returned to ammoximation zone 10 via line 15, with make-up NH$_3$ being supplied via line 16. The alcohol recovered from the ammoximation product may be recycled to zone 10 through line 18, with make-up alcohol being supplied via line 19. Cyclohexanone oxime in the form of an aqueous mixture may be withdrawn from zone 14 using line 20 and thereafter isolated by conventional techniques such as, for example, extraction into an organic solvent such as toluene followed by distillation and/or crystallization. Alternatively, the crude ammoximation product may be subjected to extraction with a suitable hydrophobic organic solvent whereby an organic phase (containing the solvent and most of the oxime) and an aqueous phase (containing water, excess NH$_3$, and most of the alcohol) are formed. The organic phase may be subsequently processed to obtain the oxime or caprolactam as may be desired and the aqueous phase recycled back to the ammoximation zone.

The acetone separated from the oxidant mixture (which may be in the form of an overhead stream) is passed via line 8 to hydrogenation zone 7 wherein the stream is reacted with hydrogen (H$_2$) introduced via line 21 in the presence of a suitable transition metal hydrogenation catalyst (introduced via a separate line or deployed as a fixed bed in zone 7) so as to convert at least a portion, and preferably substantially all, of the acetone present back to isopropanol. The hydrogenated stream produced in zone 7 is passed via line 22 to alcohol oxidation zone 1. Make-up isopropanol may be combined with the recovered and recycled isopropanol using line 23. This integrated process is preferably operated in a continuous manner such that the desired cyclohexanone oxime is the only major organic product and the acetone and isopropanol are recycled through multiple cycles.

From the foregoing description, one skilled in the art can readily ascertain the essential characteristics of this invention, and, without departing from the spirit and scope thereof, can make various changes and modifications of the invention to adapt it to various usages, conditions, and embodiments.

We claim:
1. An integrated process for producing cyclohexanone oxime comprising the steps of:
  (a) reacting isopropanol with molecular oxygen in a liquid phase at a temperature of from 50° C. to 200° C. to form an oxidant mixture comprised of isopropanol, acetone, and hydrogen peroxide;
  (b) subjecting the oxidant mixture to distillation so as to remove substantially all of the isopropanol and acetone and to provide an aqueous hydrogen peroxide stream comprised of water and hydrogen peroxide, wherein an amount of water is introduced sufficient to maintain a hydrogen peroxide concentration in the aqueous hydrogen peroxide stream less than 50% by weight;
  (c) reacting the acetone removed in step (b) with hydrogen in the presence of a heterogeneous hydrogenation catalyst wherein said hydrogenation catalyst is comprised of a transition metal selected from nickel, chromium, platinum, ruthenium, rhodium and palladium at a temperature of from 20° C. to 175° C. and a hydrogen pressure of from 0.5 to 100 atmospheres to convert the acetone to isopropanol;
  (d) reacting cyclohexanone with ammonia and the aqueous hydrogen peroxide stream at a temperature of from 25° C. to 150° C. in the presence of a catalytically effective amount of titanium silicalite and an amount of an alcohol selected from the group consisting of methanol, t-butyl alcohol and mixtures thereof sufficient to maintain a single liquid phase reaction mixture to form an ammoximation reaction product comprised of cyclohexanone oxime, water, and alcohol; and
  (e) recycling at least a portion of the isopropanol produced in step (c) for use in step (a).

2. The process of claim 1 wherein the titanium silicalite has an MFI, MEL, or zeolite beta topology.

3. The process of claim 1 wherein the titanium silicalite has a composition corresponding to the chemical formula x SiO$_2$:(1−x)TiO$_2$ wherein x is from 0.01 to 0.125.

4. The process of claim 1 wherein the titanium silicalite has a framework structure comprised of Ti, Al, and Si.

5. The process of claim 1 wherein said process is carried out continuously.

6. The process of claim 1 wherein the titanium silicalite is deployed in the form of a fixed bed.

7. The process of claim 1 comprising an additional step wherein the cyclohexanone oxime is converted to caprolactam.

8. The process of claim 1 wherein at least a portion of the isopropanol removed from the oxidant mixture in step (b) is recycled for use in step (a).

9. The process of claim 1 wherein the alcohol is separated from the ammoximation reaction product.

10. The process of claim 9 wherein at least a portion of the separated alcohol is recycled for use in step (d).

11. A continuous integrated process for producing cyclohexanone oxime comprising the steps of:
  (a) reacting isopropanol with molecular oxygen in a liquid phase at a temperature of from 100° C. to 180° C. and a partial oxygen pressure of from 1 to 50 psia to form an oxidant mixture comprised of 40 to 90 weight percent isopropanol, 5 to 35 weight percent acetone, 1 to 25 weight percent hydrogen peroxide and 0 to 35 weight percent water;
  (b) subjecting the oxidant mixture to distillation so as to remove substantially all of the isopropanol and acetone and to provide an aqueous hydrogen peroxide stream comprised of water, hydrogen peroxide, less than 1 weight percent acetone, less than 1 weight percent isopropanol and less than 0.5 weight percent ketone peroxides, wherein an amount of water is introduced sufficient to maintain the hydrogen peroxide concentration in the aqueous hydrogen peroxide stream below 50 weight %;

(c) reacting the acetone separated in step (b) with hydrogen in the presence of a heterogeneous hydrogenation catalyst wherein said hydrogenation catalyst is comprised of a transition metal selected from the group consisting of nickel and ruthenium at a temperature of from 20° to 175° C. and a molar ratio of hydrogen:acetone of from 1:1 to 4:1 to convert the acetone to isopropanol;

(d) reacting cyclohexanone with a molar excess of ammonia and the aqueous hydrogen peroxide stream at a temperature of from 50° C. to 125° C. in the presence of a catalytically effective amount of a titanium silicalite having an MFI, MEL, or zeolite beta topology and corresponding to the chemical formula $xSiO_2:(1-x)TiO_2$ wherein x is from 0.01 to 0.125 and an amount of an alcohol selected from the group consisting of methanol, t-butyl alcohol, and mixtures thereof sufficient to maintain a single liquid phase reaction mixture to form an ammoximation reaction product comprised of cyclohexanone oxime, water, and alcohol;

(e) recovering the alcohol from the ammoximation reaction product by distillation; and (f) recycling at least a portion of the isopropanol removed in step (b) and at least a portion of the isopropanol produced in step (c) for use in step (a).

12. The process of claim 11 wherein the titanium silicalite has a framework structure comprised of Ti, Al, and Si.

13. The process of claim 11 comprising an additional step wherein the cyclohexanone oxime is converted to caprolactam.

14. The process of claim 11 wherein at least a portion of the alcohol recovered in step (e) is recycled for use in step (d).

15. The process of claim 11 wherein the weight ratio of water:alcohol in step (d) is from 2:1 to 1:2.

* * * * *